United States Patent [19]

Lien et al.

[11] 4,143,158

[45] Mar. 6, 1979

[54] INHIBITION OF PROLACTIN RELEASE BY AN OPIATE ANTAGONIST

[75] Inventors: Eric L. Lien, Paoli; Donald E. Clark, Norristown, both of Pa.

[73] Assignee: American Home Products Corporation, New York, N.Y.

[21] Appl. No.: 889,774

[22] Filed: Mar. 24, 1978

[51] Int. Cl.$^2$ .......................................... A61K 31/135
[52] U.S. Cl. .................................................... 424/330
[58] Field of Search ......................................... 424/330

[56] References Cited

U.S. PATENT DOCUMENTS 3,937,818  2/1976  Fletcher et al. ..................... 424/330

*Primary Examiner*—Jerome D. Goldberg

[57] ABSTRACT

Administration of the opiate antagonist (1)-α-dimethylamino-α-(cis-2-benzoyloxycyclohexyl)-m-cresol inhibits release of prolactin without significantly inhibiting the release of growth hormone.

2 Claims, No Drawings

INHIBITION OF PROLACTIN RELEASE BY AN OPIATE ANTAGONIST

This invention relates to the chemical compound (1)-α-dimethylamino-α-(cis-2-benzoyloxycyclohexyl)-m-cresol and its use in the inhibition of prolactin release in the treatment of conditions requiring regulation of the release of such substance.

Prolactin is an important pituitary hormone whose physiological functions include the promotion of mammary gland development and the induction of lactation. Prolactin secretion is regulated by the thyrotropin releasing factor (thyroliberin or TRH) which is secreted by the hypothalamus. It is known that the administration of various substances will stimulate prolactin release: for example, the narcotic-analgesic morphine, the endogenous brain analgesic peptide methione-enkephalin, and certain methione-enkephalin analogs, have been demonstrated to effect release of prolactin. It is also known that certain substances will inhibit prolactin release: for example, the narcotic antagonist nalaxone inhibits prolactin release. [See C. Shaar et al., *Fed. Proc.*, 36, 311 (1977)]. Inhibition of prolactin release is useful in the treatment of those conditions where excessive prolactin levels are undesirable.

The invention sought to be patented constitutes a method for inhibiting prolactin release which comprises administering to said animal an effective amount of the compound (1)-α-dimethylamino-α-(cis-2-benzoyloxycyclohexyl)-m-cresol, or a non-toxic pharmaceutically acceptable acid addition salt thereof.

The compound (1)-α-dimethylamino-α-(cis-2-benzoyloxycyclohexyl)-m-cresol, employed in the method of this invention, is a narcotic antagonist. Its method of preparation and method of use as a narcotic antagonist are described in U.S. Pat. No. 3,937,818.

In carrying out the method of this invention the active compound can be administered either alone or in combination with inert pharmaceutically acceptable carriers in a variety of dosage forms, orally or parenterally. The dose requirements will vary with the severity of the conditions being presented, the animal being treated, or the dosage form employed. Therapy is instituted at low dosages and the dosage is increased incrementally until the desired prolactin-inhibiting effect is achieved.

Prolactin in blood samples can be determined by the specific double antibody radioimmunoassay method of Neill and Reichert, *Endocrinology*, 88, 548 (1971).

With large animals (about 70 kg. body weight), by the parenteral route, such as by intramuscular or subcutaneous injection, an effective dose is from about 1 mg. to about 100 mg., preferably about 5 mg. to about 20 mg.

For unit dosages, the active compound can be compounded into any of the usual oral or parenteral dosage forms, including tablets, capsules, elixir, or suspensions. The dosage forms can contain conventional inert pharmaceutical carriers as diluents, lubricating agents, stabilizing agents, preserving agents, or flavoring agents, as needed. Suitable pharmaceutical carrying agents and methods of preparation thereof will be apparent to those skilled in the art. In all cases, the proportions of the active ingredient in a dosage form must be sufficient to impart prolactin releasing activity thereto.

The ability of (1)-α-dimethylamino-α-(cis-2-benzoyloxycyclohexyl)-m-cresol to inhibit prolactin release has been demonstrated in rats as described in the following Example:

EXAMPLE

Male Charles River CD rats (300–350 g.) are given a subcutaneous injection of (1)-α-dimethylamino-α-(cis-2-benzoyloxycyclohexyl)-m-cresol in saline or of saline alone (controls). Fifteen minutes later the animals are decapitated and blood is collected in Traysylol-EDTA (12 mg. EDTA in 6000 units Traysylol). Each plasma sample is assayed for prolactin and growth hormone (GH) in triplicate by specific double antibody radioimmunoassay using NIAMDD reagents. Prolactin is determined by the method of Neill and Reichert, *Endocrinology*, 84, 548 (1971); GH is determined by the method of Sinha, *Endocrinology*, 91, 784 (1972). The results are shown in the table below:

| Treatment | Dose, mg/kg | Prolactin, ng/ml | GH, ng/ml |
|---|---|---|---|
| Saline | — | 17 ± 5 | 202 ± 22 |
| Compound | 100 | 3 ± 1* | 154 ± 23 |

Number of animals per group: 8
*$p < 0.05$

The results show that the compound (1)-α-dimethylamino-α-(cis-2-benzpyloxycyclohexyl)-m-cresol lowers serum prolactin levels in normal male rats, while not significantly lowering growth hormone.

What is claimed is:

1. A method for inhibiting prolactin release in a warm-blooded animal requiring inhibition of prolactin release which comprises administering to said animal an effective amount of the compound (1)-α-dimethylamino-α-(cis-2-benzoyloxycyclohexyl)-m-cresol, or a non-toxic pharmaceutically acceptable acid addition salt thereof.

2. A method as defined in claim 1 wherein (1)-α-dimethylamino-α-(cis-2-benzoyloxycyclohexyl)-m-cresol is in the form of the hydrochloride salt.